United States Patent
Sasaki

(10) Patent No.: US 10,857,309 B2
(45) Date of Patent: Dec. 8, 2020

(54) LIQUID MEDICINE ADMINISTRATION DEVICE

(71) Applicant: TERUMO KABUSHIKI KAISHA, Tokyo (JP)

(72) Inventor: Shohei Sasaki, Chigasaki (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 103 days.

(21) Appl. No.: 15/680,353

(22) Filed: Aug. 18, 2017

(65) Prior Publication Data

US 2017/0340841 A1  Nov. 30, 2017

Related U.S. Application Data

(63) Continuation of application No. PCT/JP2016/053589, filed on Feb. 5, 2016.

(30) Foreign Application Priority Data

Feb. 23, 2015 (JP) ................. 2015-032412

(51) Int. Cl.
*A61M 5/50* (2006.01)
*A61M 5/172* (2006.01)
(Continued)

(52) U.S. Cl.
CPC ...... *A61M 5/5086* (2013.01); *A61M 5/14248* (2013.01); *A61M 5/158* (2013.01);
(Continued)

(58) Field of Classification Search
CPC ............ A61M 5/5086; A61M 5/14248; A61M 2205/18; A61M 2205/3317; A61M 2205/359; A61M 2205/581
See application file for complete search history.

(56) References Cited

U.S. PATENT DOCUMENTS 8,147,446 B2 *  4/2012  Yodfat ............ A61M 5/14248
                                                    604/131
2008/0161754 A1  7/2008  Marano-Ford
(Continued)

FOREIGN PATENT DOCUMENTS

CN    102711868 A    10/2012
CN    103228303 A    7/2013
(Continued)

OTHER PUBLICATIONS

International Search report issued in International Patent Application No. PCT/JP2016/053589 dated Apr. 26, 2016.
(Continued)

*Primary Examiner* — Nilay J Shah
(74) *Attorney, Agent, or Firm* — Foley & Lardner LLP

(57) ABSTRACT

A portable liquid medicine administration device for continuous or intermittent administration of a liquid medicine into a living body includes: a liquid medicine administration device main body filled with the liquid medicine; and a cradle to which the liquid medicine administration device main body is attachable and detachable. The liquid medicine administration device main body includes: an alarm unit configured to output an alarm on a basis of a notification event occurring while the liquid medicine administration device main body is attached to the cradle; and an alarm control unit configured to stop the alarm on a basis of a change occurring in a relative position between the cradle and the liquid medicine administration device main body.

14 Claims, 4 Drawing Sheets

(51) Int. Cl.
*A61M 5/142* (2006.01)
*A61M 5/158* (2006.01)

(52) U.S. Cl.
CPC ..... *A61M 5/172* (2013.01); *A61M 2205/0216* (2013.01); *A61M 2205/18* (2013.01); *A61M 2205/3317* (2013.01); *A61M 2205/3569* (2013.01); *A61M 2205/581* (2013.01)

(56) References Cited

U.S. PATENT DOCUMENTS

| | | | | |
|---|---|---|---|---|
| 2010/0160759 A1* | 6/2010 | Celentano | ......... | A61B 5/14532 600/365 |
| 2011/0043357 A1* | 2/2011 | Peatfield | ............ | A61M 5/1413 340/522 |
| 2012/0203179 A1* | 8/2012 | Hills | ................. | A61M 5/16854 604/151 |
| 2014/0350485 A1* | 11/2014 | Sonderegger | ......... | A61M 5/158 604/244 |

FOREIGN PATENT DOCUMENTS

| | | |
|---|---|---|
| EP | 2 185 218 | 6/2013 |
| JP | 2004-532670 | 10/2004 |
| JP | 2009-529169 | 8/2009 |
| JP | 2013-537844 | 10/2013 |
| JP | 2014-000432 | 1/2014 |
| WO | WO-2009/016635 | 2/2009 |

OTHER PUBLICATIONS

Chinese Office Action dated Nov. 15, 2019 for corresponding Application No. 201680005125.0.

* cited by examiner

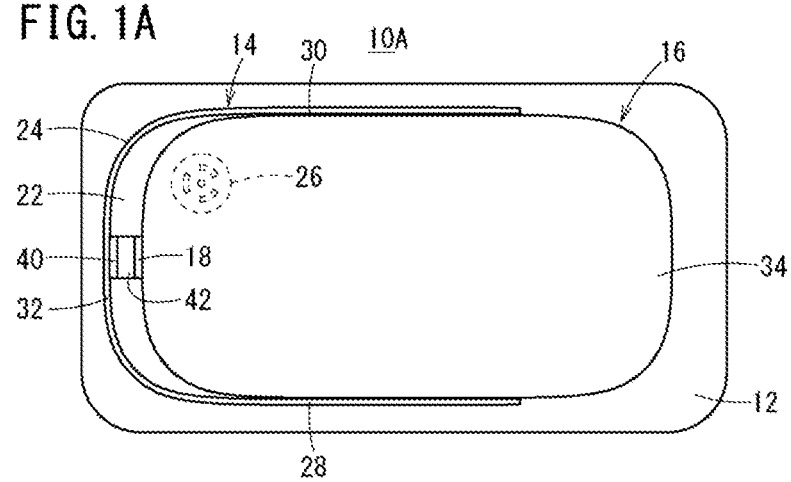
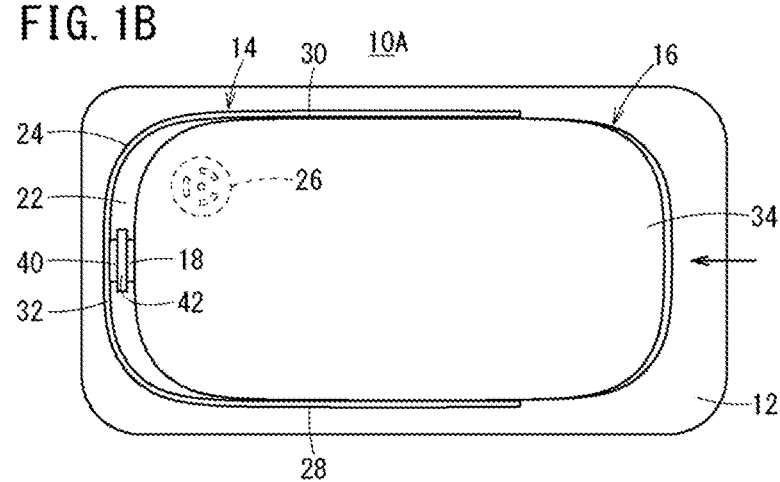
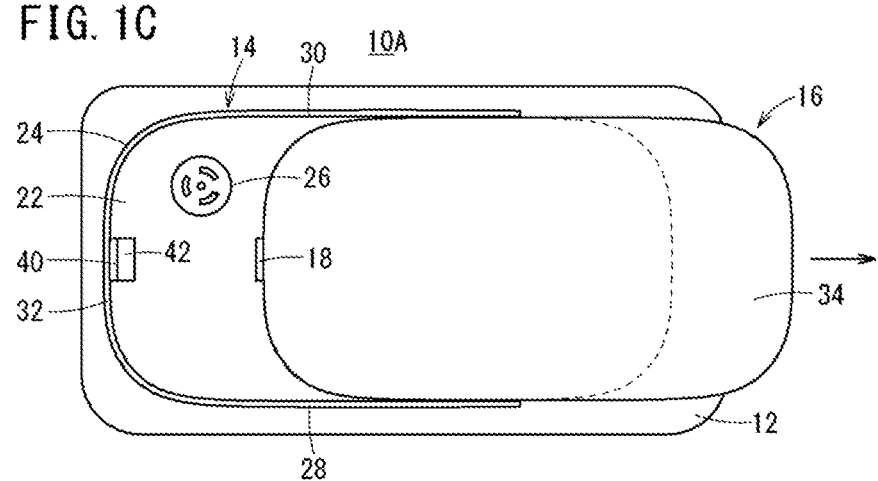

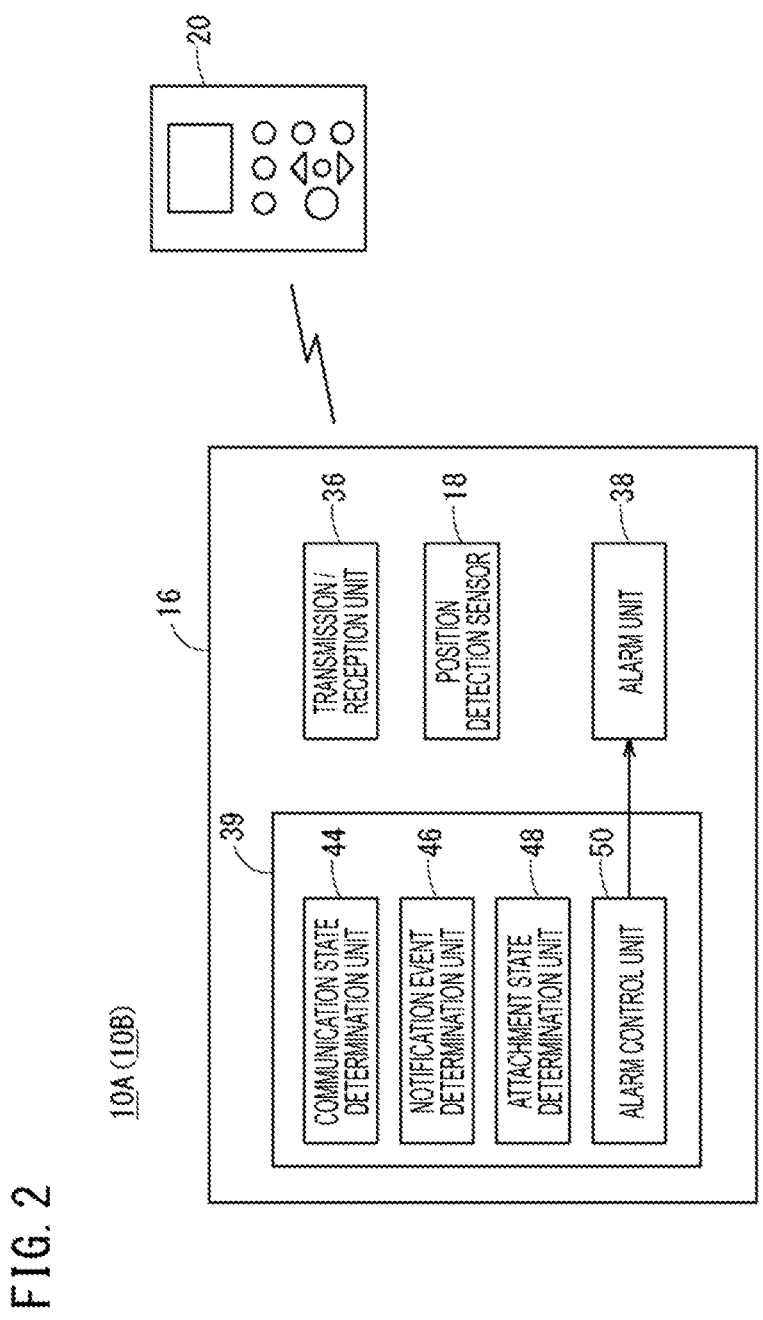

LIQUID MEDICINE ADMINISTRATION DEVICE

CROSS-REFERENCE TO RELATED APPLICATIONS

The present application is a bypass continuation of PCT Application No. PCT/JP2016/053589, filed on Feb. 5, 2016, which claims priority to Japanese Application No. 2015-032412, filed on Feb. 23, 2015. The contents of these application are hereby incorporated by reference in their entireties.

BACKGROUND

The present application relates to a portable liquid medicine administration device for continuous or intermittent administration of a liquid medicine filled in a liquid medicine administration device main body into a living body.

Background Art

As this type of the liquid medicine administration device, for example, European Patent No. 2185218 discloses a technical idea in which a liquid medicine administration device main body is attached to a cradle adhered to the skin of a user, and is driven to be controlled using a remote controller.

SUMMARY

An alarm unit that outputs an alarm such as an alarm sound on the basis of a notification event may be provided in a liquid medicine administration device main body. In addition, such an alarm is normally stopped by operation of a remote controller.

However, a user does not necessarily carry the remote controller at all times, and there are cases in which the remote controller is not at hand or cannot be found. In such cases, it is possible that the alarm of the alarm unit cannot be stopped for a long time.

The concepts described in this application have been developed in consideration of such a problem, and one object of certain embodiments described in this application is to provide a liquid medicine administration device capable of easily and quickly stopping an alarm of an alarm unit of a liquid medicine administration device main body without operation of a remote controller.

In one embodiment, a liquid medicine administration device is a portable liquid medicine administration device for continuous or intermittent administration of a liquid medicine into a living body. The device includes: a liquid medicine administration device main body filled with the liquid medicine; and a cradle to which the liquid medicine administration device main body is detachably attached, in which the liquid medicine administration device main body includes: an alarm unit that outputs an alarm on the basis of a notification event in a state of being attached to the cradle; and an alarm control unit that stops the alarm on the basis of a change in a relative position between the cradle and the liquid medicine administration device main body.

According to this embodiment, a user can easily and quickly stop, without operating a remote controller, the alarm of the alarm unit by changing the relative position between the cradle and the liquid medicine administration device main body.

The above-described liquid medicine administration device may further include a notification event determination unit that determines whether the notification event is an emergency notification event or a normal notification event, and in a case where the notification event determination unit determines that the notification event is the emergency notification event, the alarm control unit may stop the alarm on the basis that the liquid medicine administration device main body has been detached from the cradle, and the alarm control unit may not stop the alarm on the basis of operation of the liquid medicine administration device main body other than the operation that the liquid medicine administration device main body has been detached from the cradle.

According to such a configuration, the user can reliably stop the alarm relating to the emergency notification event without operating the remote controller, while suppressing that the alarm relating to the emergency notification event is unintentionally stopped when the user touches the liquid medicine administration device main body.

In the above-described liquid medicine administration device, in a case where the notification event determination unit determines that the notification event is the normal notification event, the alarm control unit may stop the alarm on the basis that the liquid medicine administration device main body has been detached from the cradle, or that the liquid medicine administration device main body has been pushed in an attachment direction with respect to the cradle.

According to such a configuration, the alarm relating to the normal notification event can be stopped by simple operation of the liquid medicine administration device main body.

In the above-described liquid medicine administration device, in a case where the notification event determination unit determines that the notification event is the emergency notification event, the liquid medicine administration device main body may stop delivery of the liquid medicine.

According to such a configuration, it is possible to suppress that the liquid medicine is administered into the living body when the emergency notification event occurs.

The above-described liquid medicine administration device may include: a position detection sensor that detects a position of the liquid medicine administration device main body with respect to the cradle; and an attachment state determination unit that determines, on the basis of an output signal from the position detection sensor, whether or not the liquid medicine administration device main body has been detached from the cradle, and whether or not the liquid medicine administration device main body has been pushed in the attachment direction with respect to the cradle.

According to such a configuration, it is possible to reliably determine whether or not the liquid medicine administration device main body has been detached from the cradle, and whether or not the liquid medicine administration device main body has been pushed in the attachment direction with respect to the cradle.

In the above-described liquid medicine administration device, a magnet may be provided to one of the liquid medicine administration device main body and the cradle, and the position detection sensor may be provided to the other one of the liquid medicine administration device main body and the cradle to detect a magnetic field of the magnet.

According to such a configuration, the position of the liquid medicine administration device main body with respect to the cradle can be detected with a simple configuration.

In the above-described liquid medicine administration device, in a state where the liquid medicine administration device main body is attached to the cradle, the magnet and the position detection sensor may be opposed to each other along the attachment direction of the liquid medicine administration device main body.

According to such a configuration, the attachment state determination unit can determine, on the basis of the output signal from one position detection sensor, whether or not the liquid medicine administration device main body has been detached from the cradle, and whether or not the liquid medicine administration device main body has been pushed in the attachment direction with respect to the cradle.

The above-described liquid medicine administration device may include an elastic member that returns the liquid medicine administration device main body pushed in the attachment direction with respect to the cradle to an original position.

According to such a configuration, the liquid medicine administration device main body pushed in the attachment direction with respect to the cradle can be automatically returned to the original position.

According to certain embodiments described in this application, by changing the relative position between the cradle and the liquid medicine administration device main body, the alarm of the alarm unit of the liquid medicine administration device main body can be easily and quickly stopped without operation of the remote controller.

BRIEF DESCRIPTION OF THE DRAWINGS

FIG. 1A is a plan view illustrating a first state of a liquid medicine administration device according to a first embodiment of the present invention, FIG. 1B is a plan view illustrating a second state of the liquid medicine administration device, and FIG. 1C is a plan view illustrating a third state of the liquid medicine administration device.

FIG. 2 is a control block diagram of the liquid medicine administration device.

DETAILED DESCRIPTION

Figure 3:
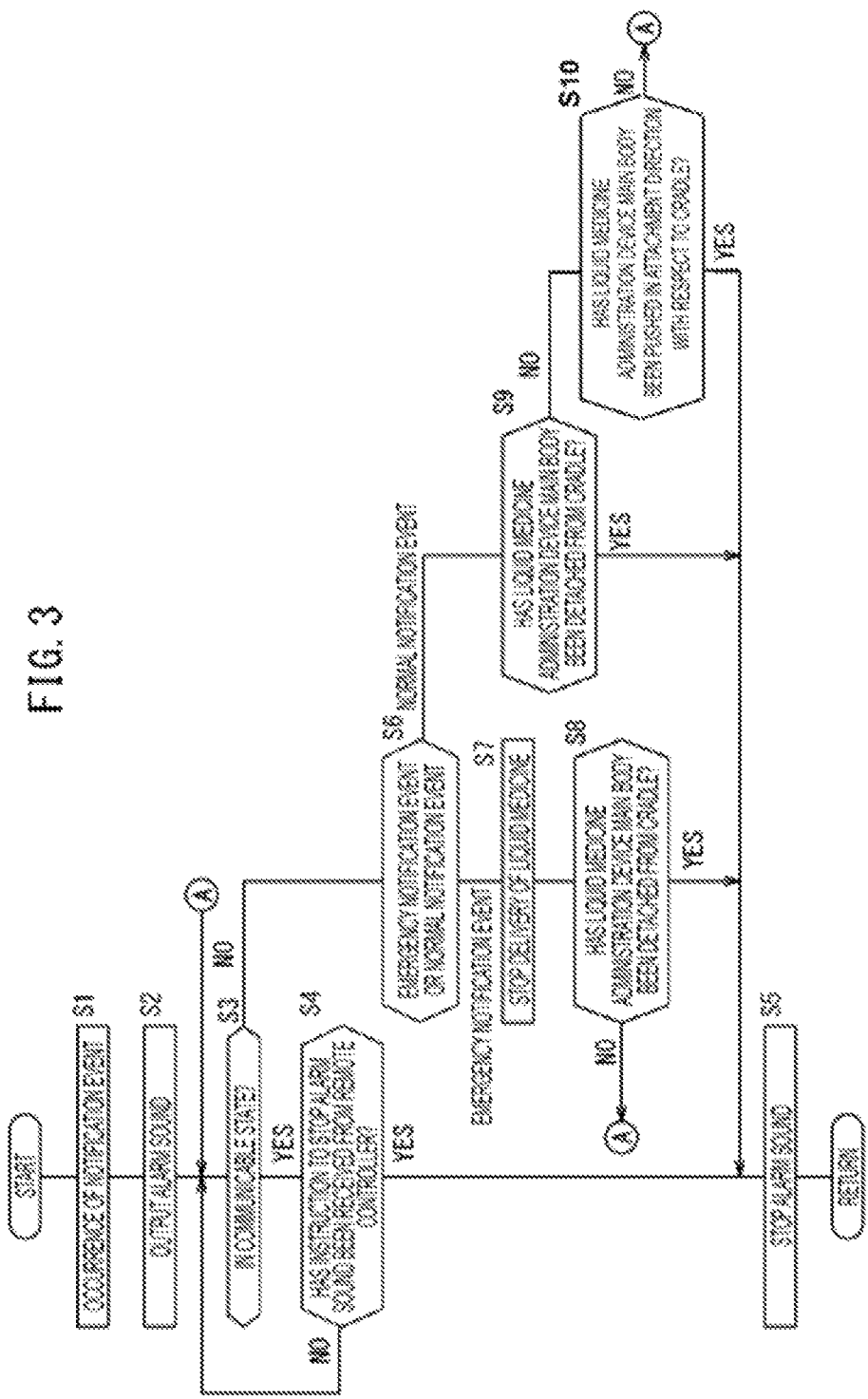
FIG. 3 is a flowchart explaining operation of the liquid medicine administration device.

Embodiments of a liquid medicine administration device according to the present invention are described below with reference to the accompanying drawings.

First Embodiment

A liquid medicine administration device 10A according to the present embodiment is a portable liquid medicine administration device 10A that continuously or intermittently administers a liquid medicine filled in a liquid medicine administration device main body 16 into the living body, and is configured as a patch-type insulin pump. Note that the liquid medicine administration device 10A is not limited to that of the patch type, but may be of a tube type or the like.

As illustrated in FIGS. 1A and 2, the liquid medicine administration device 10A includes a cradle 14 provided with a seal portion 12 that can be adhered to the skin of a user (patient), a liquid medicine administration device main body 16 that can be detachably located in the cradle 14, a position detection sensor 18 that detects a position of the liquid medicine administration device main body 16 with respect to the cradle 14, and a remote controller 20.

The cradle 14 is a holder (holding member) that can be fixed to the user and to which the liquid medicine administration device main body 16 is detachably attached. The cradle 14 is integrally formed of a resin material, and includes a substantially rectangular support plate 22 to which the seal portion 12 is stuck, and a side wall 24 provided to an outer peripheral edge portion of the support plate 22.

A cannula mechanism 26 having a cannula is attached to a corner portion of the support plate 22. Note that, in an initial state of the cradle 14, the cannula mechanism 26 is not attached to the cradle 14, and is held by a puncture mechanism which is not illustrated. When the puncture mechanism is operated, as the cannula mechanism 26 including the cannula moves to a side of the living body, the cannula is punctured to the living body, and the cannula mechanism 26 is fixed (attached) to the cradle 14. The side wall 24 is formed in a substantially U shape in a plan view, and includes a pair of opposite walls 28, 30 opposed to each other, and a connection wall 32 that connects these opposite walls 28, 30.

The liquid medicine administration device main body 16 is attached to the cradle 14 by being slid toward the connection wall 32 along a longitudinal direction of the support plate 22, and is detached from the cradle 14 by being slid in a direction away from the connection wall 32 along the longitudinal direction of the support plate 22 (see FIG. 1C). Further, the liquid medicine administration device main body 16 can be pushed in the attachment direction (toward the connection wall 32) with respect to the cradle 14, in a state of being attached to the cradle 14 (see FIG. 1B).

The liquid medicine administration device main body 16 includes a housing 34 which is substantially rectangular in a plan view. Although an internal structure of the housing 34 is not illustrated in FIGS. 1A to 1C, a barrel filled with the liquid medicine, a plunger provided in the barrel, a drive unit that drives the plunger, and an outlet tube that guides the liquid medicine in the barrel to the cannula mechanism 26 are disposed in the housing 34. In addition, the cannula and the outlet tube communicate with each other in a state where the liquid medicine administration device main body 16 is attached to the cradle 14, so that the liquid medicine in the barrel can be administered into the living body under pressing operation of the plunger.

The position detection sensor 18 is configured as a magnetic sensor such as a Hall element, for example, and is provided to the housing 34 so as to oppose to a magnet 40 provided to the connection wall 32 in a state where the liquid medicine administration device main body 16 is attached to the cradle 14. That is, the position detection sensor 18 detects the position of the liquid medicine administration device main body 16 with respect to the cradle 14 by detecting a magnetic field of the magnet 40.

Note that, in the present embodiment, the magnet 40 may be provided to the housing 34, and the position detection sensor 18 may be provided to the connection wall 32 so as to oppose to the magnet 40. Even in this case, the position detection sensor 18 can preferably detect the magnetic field of the magnet 40.

The magnet 40 is provided with an elastic member 42 that returns the liquid medicine administration device main body 16 pushed toward the connection wall 32 to the original position. By providing such an elastic member 42, the liquid medicine administration device main body 16 pushed in the attachment direction with respect to the cradle 14 can be automatically returned to the original position. That is, the user does not need to manually return the liquid medicine administration device main body 16 pushed in the attachment direction with respect to the cradle 14 to the original position.

Note that the elastic member 42 can be provided at arbitrary positions of the position detection sensor 18, the housing 34, and the cradle 14. When the elastic member 42 is provided at a position other than a position between the magnet 40 and the position detection sensor 18, the position detection sensor 18 can efficiently detect the magnetic field of the magnet 40. Further, the elastic member 42 can be made of rubber, a spring, or the like.

As illustrated in FIG. 2, the liquid medicine administration device main body 16 includes a transmission/reception unit 36 that performs information communication with the remote controller 20, an alarm unit 38 that outputs an alarm sound, and a control unit 39.

The alarm unit 38 outputs the alarm sound on the basis of occurrence of a notification event. It should be noted that the alarm unit 38 may be configured to output an emergency alarm sound and a normal alarm sound according to urgency of the notification event. In this case, at least one of a frequency, an amplitude, an output time, and the number of times of output of each of the emergency alarm sound and the normal alarm sound is different so that the user can easily distinguish the emergency alarm sound and the normal alarm sound from each other. Note that, in the present embodiment, the alarm unit 38 outputs the same alarm sound regardless of the urgency of the notification event.

The control unit 39 includes a communication state determination unit 44, a notification event determination unit 46, an attachment state determination unit 48, and an alarm control unit 50. The communication state determination unit 44 determines whether or not the transmission/reception unit 36 and the remote controller 20 are in a communicable state.

The notification event determination unit 46 determines whether the occurred notification event is an emergency notification event or a normal notification event. Here, examples of the emergency notification event include an event that notifies a user about occlusion of the cannula and an event that notifies a user that the liquid medicine is empty. Examples of the normal notification event include an event of providing an alarm at a preset time, an event that notifies a user of a bolus administration time, and an event that notifies a user of a decrease in a residual amount of the liquid medicine.

On the basis of an output signal from the position detection sensor 18, the attachment state determination unit 48 determines whether or not the liquid medicine administration device main body 16 has been pushed in the attachment direction with respect to the cradle 14, and whether or not the liquid medicine administration device main body 16 has been detached from the cradle 14. Specifically, in a case where the output signal from the position detection sensor 18 (magnitude of the detected magnetic field) is smaller than a first threshold value, the attachment state determination unit 48 determines that the liquid medicine administration device main body 16 has been detached from the cradle 14. Further, in a case where the output signal from the position detection sensor 18 is larger than a second threshold value, the attachment state determination unit 48 determines that the liquid medicine administration device main body 16 has been pushed in the attachment direction with respect to the cradle 14. The second threshold value is normally set larger than the first threshold value.

The alarm control unit 50 stops the alarm sound on the basis of determination results of the notification event determination unit 46 and the attachment state determination unit 48. Specifically, the alarm control unit 50 stops the alarm sound in a case where the notification event determination unit 46 determines that the occurred notification event is the emergency notification event, and the attachment state determination unit 48 determines that the liquid medicine administration device main body 16 has been detached from the cradle 14.

Further, the alarm control unit 50 stops the alarm sound in a case where the notification event determination unit 46 determines that the occurred notification event is the normal notification event, and the attachment state determination unit 48 determines that the liquid medicine administration device main body 16 has been detached from the cradle 14, or the liquid medicine administration device main body 16 has been pushed in the attachment direction with respect to the cradle 14.

The liquid medicine administration device 10A according to the present embodiment is basically configured as described above, and hereinbelow, operation and effects of the liquid medicine administration device 10A will be described.

The user adheres the cradle 14 to the skin of the user by the seal portion 12 and the cannula is indwelled in the living body by the puncture mechanism which is not illustrated, so that the liquid medicine administration device main body 16 in which the barrel is filled with the liquid medicine is attached to the cradle 14 (see FIG. 1A). Then, by operation of the remote controller 20, the liquid medicine in the liquid medicine administration device main body 16 is continuously or intermittently administered into the living body.

When a notification event occurs during such administration of the liquid medicine (step S1 in FIG. 3), the alarm unit 38 outputs an alarm sound (step S2). Then, the communication state determination unit 44 determines whether or not the transmission/reception unit 36 of the liquid medicine administration device main body 16 and the remote controller 20 are in a communicable state (step S3).

In a case where the transmission/reception unit 36 and the remote controller 20 are in the communicable state (step S3: YES), the control unit 39 determines whether or not an instruction to stop the alarm sound is received from the remote controller 20 (step S4).

In a case where the instruction to stop the alarm sound is not received, processes after step S3 are performed, and in a case where the instruction to stop the alarm sound is received, the alarm control unit 50 stops the alarm sound (step S5). Then, this flowchart is terminated.

In a case where the communication state determination unit 44 determines that the transmission/reception unit 36 and the remote controller 20 are not in the communicable state in step S3 (step S3: NO), the notification event determination unit 46 determines whether the occurred notification event is an emergency notification event or a normal notification event (step S6).

In a case where the notification event determination unit 46 determines that the occurred notification event is the emergency notification event, the liquid medicine administration device main body 16 stops delivery of the liquid medicine (step S7). Accordingly, it is possible to suppress that the liquid medicine is administered into the living body when the emergency notification event occurs. Note that step S7 is executed only in a case where the liquid medicine is being delivered by the liquid medicine administration device main body 16.

Subsequently, the attachment state determination unit 48 determines whether or not the liquid medicine administration device main body 16 has been detached from the cradle 14 on the basis of the output signal from the position detection sensor 18 (step S8). In a case where the liquid medicine administration device main body 16 has not been detached from the cradle 14 (step S8: NO), the processes after step S3 are performed.

In a case where the liquid medicine administration device main body 16 has been detached from the cradle 14 (see FIG. 1C, step S8: YES), the alarm control unit 50 stops the alarm sound, and then this flowchart is terminated.

In this way, in a case where the occurred notification event is the emergency notification event, the alarm control unit 50 stops the alarm sound on the basis that the liquid medicine administration device main body 16 has been detached from the cradle 14, and the alarm control unit 50 does not stop the alarm sound on the basis of operation of the liquid medicine administration device main body 16 other than the operation that the liquid medicine administration device main body 16 has been from the cradle 14. Accordingly, the user can reliably stop the alarm sound relating to the emergency notification event of the alarm unit 38 without operating the remote controller 20, while suppressing that the alarm sound relating to the emergency notification event is unintentionally stopped when the user touches the liquid medicine administration device main body 16.

On the other hand, in a case where the notification event determination unit 46 determines that the occurred notification event is the normal notification event in step S6, the attachment state determination unit 48 determines whether or not the liquid medicine administration device main body 16 has been detached from the cradle 14 on the basis of the output signal from the position detection sensor 18 (step S9). In a case where the liquid medicine administration device main body 16 has been detached from the cradle 14 (step S9: YES), the alarm control unit 50 stops the alarm sound, and then this flowchart is terminated.

In a case where the liquid medicine administration device main body 16 has not been detached from the cradle 14 (step S9: NO), the attachment state determination unit 48 determines whether or not the liquid medicine administration device main body 16 has been pushed in the attachment direction with respect to the cradle (step S10).

In a case where the liquid medicine administration device main body 16 has not been pushed in the attachment direction with respect to the cradle 14 (step S10: NO), the processes after step S3 are performed, and in a case where the liquid medicine administration device main body 16 has been pushed in the attachment direction with respect to the cradle 14 (see FIG. 1B, step S10: YES), after the alarm control unit 50 stops the alarm sound, this flowchart is terminated.

In this way, in a case where the occurred notification event is the normal notification event, the alarm control unit 50 stops the alarm sound on the basis that the liquid medicine administration device main body 16 has been detached from the cradle 14 or the liquid medicine administration device main body 16 has been pushed in the attachment direction with respect to the cradle 14. Therefore, the alarm sound related to the normal notification event can be stopped by simple operation of the liquid medicine administration device main body 16.

According to the present embodiment, the user can easily and quickly stop, without operating the remote controller 20, the alarm sound of the alarm unit 38 by changing the relative position between the cradle 14 and the liquid medicine administration device main body 16.

In the present embodiment, the magnetic field of the magnet 40 provided in the cradle 14 is detected by the position detection sensor 18 provided in the liquid medicine administration device main body 16. Therefore, the position of the liquid medicine administration device main body 16 with respect to the cradle 14 can be detected with a simple configuration.

Further, in a state where the liquid medicine administration device main body 16 is attached to the cradle 14, the magnet 40 and the position detection sensor 18 are opposed to each other along the attachment direction. Therefore, the attachment state determination unit 48 can determine, on the basis of the output signal from one position detection sensor 18, whether or not the liquid medicine administration device main body 16 has been detached from the cradle 14, and whether or not the liquid medicine administration device main body 16 has been pushed in the attachment direction of the cradle 14.

In the present embodiment, in the flowchart of FIG. 3 described above, step S3 may be omitted, and the processes after step S6 may be performed in a case where the instruction to stop the alarm sound from the remote controller 20 is not received in step S4.

Accordingly, regardless of whether or not the transmission/reception unit 36 of the liquid medicine administration device main body 16 and the remote controller 20 are in the communicable state, the alarm sound of the alarm unit 38 of the liquid medicine administration device main body 16 can be easily and quickly stopped without operation of the remote controller 20 in a case where the remote controller 20 is not at hand or not found.

Second Embodiment

Next, a liquid medicine administration device 10B according to a second embodiment of the present invention will be described. Note that, in the liquid medicine administration device 10B according to the second embodiment, the same components as those of the liquid medicine administration device 10A according to the first embodiment are denoted by the same reference signs, and a detailed description thereof will be omitted.

Figure 4A:
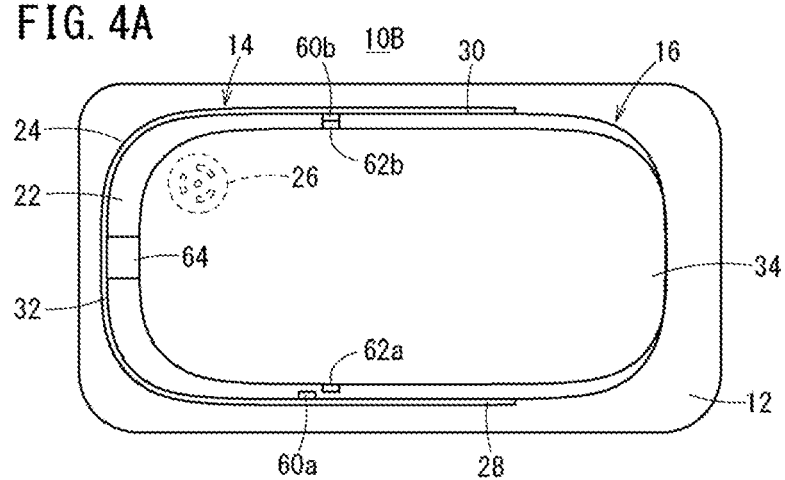
FIG. 4A is a plan view illustrating a first state of a liquid medicine administration device according to a second embodiment of the present invention.

As illustrated in FIG. 4A, in the liquid medicine administration device 10B, a pair of magnets 60a, 60b is provided in the cradle 14 and a pair of position detection sensors 62a, 62b is provided in the liquid medicine administration device main body 16. The magnet 60a is provided to one opposite wall 28, and the magnet 60b is provided to the other opposite wall 30.

Figure 4B:
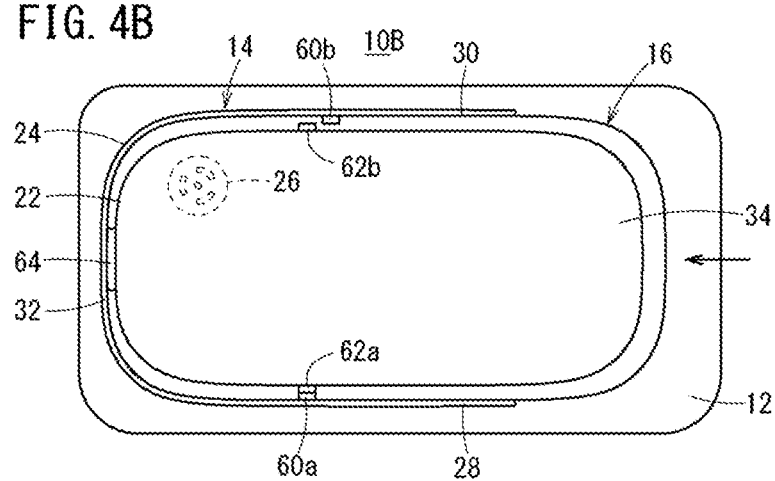
FIG. 4B is a plan view illustrating a second state of the liquid medicine administration device.
Figure 4C:
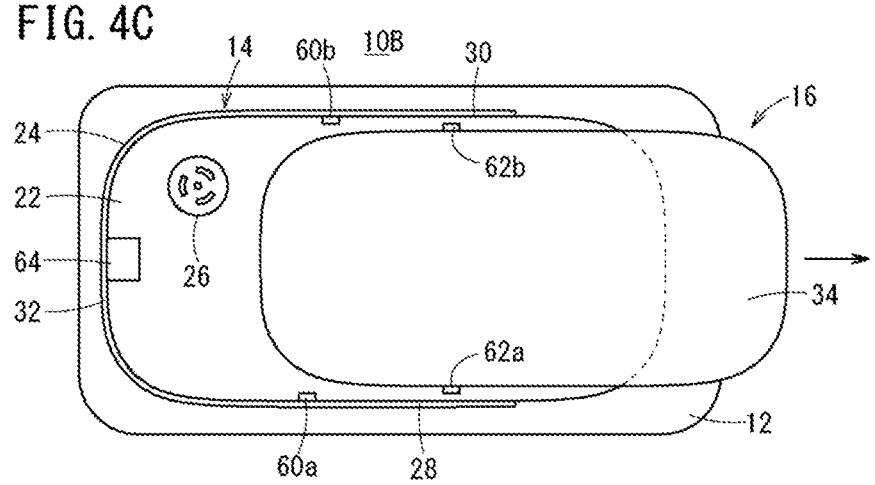
FIG. 4C is a plan view illustrating a third state of the liquid medicine administration device.

The position detection sensors 62a, 62b are configured similarly to the above-described position detection sensor 18. The position detection sensor 62a is opposed to the magnet 60a in a state where the liquid medicine administration device main body 16 is pushed in the attachment direction along the longitudinal direction of the support plate 22 (see FIG. 4B).

The position detection sensor 62b is opposed to the magnet 60b in a state where the liquid medicine administration device 10B is attached to the cradle 14 (a state where the liquid medicine administration device main body 16 is not pushed in) (see FIG. 4A).

The attachment state determination unit 48 determines that the liquid medicine administration device main body 16 has been pushed in the attachment direction with respect to the cradle 14 in a case where a magnetic field of the magnet 60a is detected by the position detection sensor 62a and a magnetic field of the magnet 60b is not detected by the position detection sensor 62b. Further, the attachment state determination unit 48 determines that the liquid medicine administration device main body 16 has been detached from the cradle 14 in a case where the magnetic field of the magnet 60a is not detected by the position detection sensor 62a and the magnetic field of the magnet 60b is not detected by the position detection sensor 62b.

Note that the connection wall 32 of the cradle 14 is provided with an elastic member 64 for returning the liquid medicine administration device main body 16 that has been pushed, to its original attachment position. The elastic member 64 is configured similarly to the above-described elastic member 42.

The liquid medicine administration device 10B according to the present embodiment exerts the operation and effect similar to those of the above-described liquid medicine administration device 10A. In the present embodiment, the position detection sensor 62a may be provided to the one opposite wall 28 and the position detection sensor 62b may be provided to the other opposite wall 30, and the magnets 60a, 60b corresponding to these position detection sensors 62a, 62b may be provided to the liquid medicine administration device main body 16. Further, the position detection sensors 62a, 62b may be configured as microswitches (switch units), and a switch operation member capable of operating the microswitches may be provided instead of the magnets 60a, 60b.

In the above-described liquid medicine administration devices 10A, 10B, the alarm control unit 50 may stop the alarm sound of the alarm unit 38 by, for example, pushing the liquid medicine administration device main body 16 toward a side of the support plate 22 to change the relative position between the liquid medicine administration device main body 16 and the cradle 14.

Further, in a case where the alarm control unit 50 stopped the alarm sound of the alarm unit 38 by changing the relative position between the cradle 14 and the liquid medicine administration device main body 16, the alarm control unit 50 may output the alarm sound again from the alarm unit 38 after a predetermined time has elapsed since the alarm sound was stopped (snooze operation may be performed). In this case, the alarm control unit 50 may stop the snooze operation in a case where the instruction to stop the alarm sound is received from the remote controller 20. Accordingly, a content of the notification event can be confirmed by the user via the remote controller 20.

Further, although the position detection sensors 18, 62a, 62b are disposed outside the housing 34 of the liquid medicine administration device main body 16 in the above-described liquid medicine administration devices 10A, 10B, the position detection sensors 18, 62a, 62b may be disposed inside the housing 34 so as to detect the magnetic fields.

Furthermore, in the above-described embodiment, the alarm unit 38 is not limited to the example of outputting the alarm sound, and notification to the user may be made by output of sound, lighting or blinking of an indicator lamp, displaying a character, vibration, or the like.

What is claimed is:
1. A portable liquid medicine administration device for continuous or intermittent administration of a liquid medicine into a living body, the device comprising:
   a liquid medicine administration device main body filled with the liquid medicine;
   a remote controller configured to perform communication with the liquid medicine administration device main body; and
   a cradle to which the liquid medicine administration device main body is attachable and detachable,
   wherein the liquid medicine administration device main body comprises:
     an alarm unit configured to output an alarm on a basis of a notification event occurring while the liquid medicine administration device main body is attached to the cradle, wherein the notification event comprises at least one of (i) an event to notify a user about occlusion of a cannula of the liquid medicine administration device, (ii) an event to notify the user that the liquid medicine is empty, (iii) an event to provide the alarm at a preset time, (iv) an event to notify the user of a bolus administration time, or (v) an event to notify the user of a decrease in a residual amount of the liquid medicine,
     a communication state determination unit configured to determine whether or not the liquid medicine administration device main body and the remote controller are in a communicable state,
     a notification event determination unit configured to determine whether the notification event is an emergency notification event or a normal notification event, wherein the emergency notification event comprises at least one of (i) the event to notify the user about occlusion of the cannula of the liquid medicine administration device, or (ii) the event to notify the user that the liquid medicine is empty, and wherein the normal notification event comprises at least one of (iii) the event to provide the alarm at the preset time, (iv) the event to notify the user of the bolus administration time, or (v) the event to notify the user of the decrease in the residual amount of the liquid medicine,
     a position detection sensor configured to detect a position of the liquid medicine administration device main body with respect to the cradle,
     an attachment state determination unit configured to determine, on a basis of an output signal from the position detection sensor, whether or not the liquid medicine administration device main body has been detached from the cradle, and whether or not the liquid medicine administration device main body has been pushed in an attachment direction with respect to the cradle, and
     an alarm control unit configured to, in a case where the liquid medicine administration device main body and the remote controller are not in the communicable state and the notification event determination unit determines that the notification event is the normal notification event, stop the alarm at least when the attachment state determination unit determines that, while the liquid medicine administration device main body is attached to the cradle, the liquid medicine administration device main body has been pushed in the attachment direction with respect to the cradle.

2. The liquid medicine administration device according to claim 1, wherein:
   the alarm control unit is configured to, in a case where the notification event determination unit determines that the notification event is an emergency notification event, stop the alarm when the attachment state determination unit determines that the liquid medicine administration device main body is detached from the cradle, and to not stop the alarm when an operation of the liquid medicine administration device main body occurs other than the liquid medicine administration device main body being detached from the cradle.

3. The liquid medicine administration device according to claim 2, wherein:
the alarm control unit is configured to, in the case where the notification event determination unit determines that the notification event is the normal notification event, stop the alarm when the attachment state determination unit determines that the liquid medicine administration device main body is detached from the cradle.

4. The liquid medicine administration device according to claim 2, wherein:
in the case where the notification event determination unit determines that the notification event is the emergency notification event, the liquid medicine administration device main body stops delivery of the liquid medicine.

5. The liquid medicine administration device according to claim 1, wherein:
a magnet is located in one of the liquid medicine administration device main body and the cradle, and
the position detection sensor is located in the other one of the liquid medicine administration device main body and the cradle, the position detection sensor being configured to detect a magnetic field of the magnet.

6. The liquid medicine administration device according to claim 5, wherein:
in a state where the liquid medicine administration device main body is attached to the cradle, the magnet and the position detection sensor are opposed to each other along the attachment direction of the liquid medicine administration device main body.

7. The liquid medicine administration device according to claim 1, further comprising:
an elastic member configured to return the liquid medicine administration device main body pushed in the attachment direction with respect to the cradle to an original position.

8. A method for stopping an alarm of a liquid medicine administration device, the method comprising:
providing the liquid medicine administration device, which comprises:
a liquid medicine administration device main body filled with a liquid medicine, wherein the liquid medicine administration device main body comprises an alarm unit, a communication state determination unit, a notification event determination unit, a position detection sensor, an attachment state determination unit, and an alarm control unit,
a remote controller configured to perform communication with the liquid medicine administration device main body, and
a cradle to which the liquid medicine administration device main body is attachable and detachable;
outputting the alarm using the alarm unit on a basis of a notification event occurring while the liquid medicine administration device main body is attached to the cradle, wherein the notification event comprises at least one of (i) an event to notify a user about occlusion of a cannula of the liquid medicine administration device, (ii) an event to notify the user that the liquid medicine is empty, (iii) an event to provide the alarm at a preset time, (iv) an event to notify the user of a bolus administration time, or (v) an event to notify the user of a decrease in a residual amount of the liquid medicine;
determining, using the communication state determination unit, whether or not the liquid medicine administration device main body and the remote controller are in a communicable state;
determining, using a notification event determination unit, whether the notification event is an emergency notification event or a normal notification event, wherein the emergency notification event comprises at least one of (i) the event to notify the user about occlusion of the cannula of the liquid medicine administration device, or (ii) the event to notify the user that the liquid medicine is empty, and wherein the normal notification event comprises at least one of (iii) the event to provide the alarm at the preset time, (iv) the event to notify the user of the bolus administration time, or (v) the event to notify the user of the decrease in the residual amount of the liquid medicine;
detecting, using the position detection sensor, a position of the liquid medicine administration device main body with respect to the cradle;
determining, using the attachment state determination unit, on a basis of an output signal from the position detection sensor, whether or not the liquid medicine administration device main body has been detached from the cradle, and whether or not the liquid medicine administration device main body has been pushed in an attachment direction with respect to the cradle; and
in a case where the liquid medicine administration device main body and the remote controller are not in the communicable state and the notification event determination unit determines that the notification event is the normal notification event, stopping the alarm using the alarm control unit at least when the attachment state determination unit determines that, while the liquid medicine administration device main body is attached to the cradle, the liquid medicine administration device main body has been pushed in the attachment direction with respect to the cradle.

9. The method according to claim 8, comprising:
in a case where the notification event determination unit determines that the notification event is an emergency notification event, stopping the alarm using the alarm control unit when the attachment state determination unit determines that the liquid medicine administration device main body is detached from the cradle, and not stopping the alarm using the alarm control unit when an operation of the liquid medicine administration device main body occurs other than the liquid medicine administration device main body being detached from the cradle.

10. The method according to claim 9, comprising:
in the case where the notification event determination unit determines that the notification event is the normal notification event, stopping the alarm using the alarm control unit when the attachment state determination unit determines that the liquid medicine administration device main body is detached from the cradle.

11. The method according to claim 9, comprising:
in the case where the notification event determination unit determines that the notification event is the emergency notification event, stopping delivery of the liquid medicine using the liquid medicine administration device main body.

12. The method according to claim 8, wherein:
a magnet is located in one of the liquid medicine administration device main body and the cradle, and
the position detection sensor is located in the other one of the liquid medicine administration device main body and the cradle, the position detection sensor being configured to detect a magnetic field of the magnet.

13. The method according to claim 12, wherein:
in a state where the liquid medicine administration device main body is attached to the cradle, the magnet and the position detection sensor are opposed to each other along the attachment direction of the liquid medicine administration device main body.

14. The method according to claim 8, further comprising:
an elastic member configured to return the liquid medicine administration device main body pushed in the attachment direction with respect to the cradle to an original position.

\* \* \* \* \*